United States Patent [19]

Noguchi et al.

[11] Patent Number: 4,662,212
[45] Date of Patent: May 5, 1987

[54] MEASURING INSTRUMENT FOR CONCENTRATION OF GAS

[75] Inventors: Yasuo Noguchi, Yokohama; Morito Idemoto, Tokyo; Fumiaki Matsunaga, Yokohama, all of Japan

[73] Assignee: Sumitomo Bakelite Company Limited, Tokyo, Japan

[21] Appl. No.: 752,535

[22] Filed: Jul. 8, 1985

[30] Foreign Application Priority Data

Sep. 10, 1984 [JP] Japan .................. 59-188018
May 23, 1985 [JP] Japan .................. 60-109420

[51] Int. Cl.$^4$ ............................ G01N 29/02
[52] U.S. Cl. ........................ 73/24; 310/340; 310/344
[58] Field of Search ............. 73/24, 30, 32 A; 310/340, 344, 334, 336

[56] References Cited

U.S. PATENT DOCUMENTS 2,513,870  7/1950  Hoffman .................. 310/344
2,769,930  11/1956  Sturm ..................... 310/340
2,785,321  3/1957  Imler ...................... 310/344
4,117,716  10/1978  Simon ..................... 73/32 A
4,220,040  9/1980  Noguchi et al. ............. 73/24

FOREIGN PATENT DOCUMENTS 47-6797  2/1972  Japan .
48-34535  5/1973  Japan .

OTHER PUBLICATIONS

Journal of the Acoustical Society of Japan, vol. 32, No. 7, Jul. 1976, pp. 436–442.
J. Acoust. Soc. Am., vol. 63 (6), Jun. 1978, Chen, et al., pp. 1795–1800.

Primary Examiner—Stephen A. Kreitman
Attorney, Agent, or Firm—Browdy and Neimark

[57] ABSTRACT

A gas concentration measuring instrument using the dependency of the propagation velocity of ultrasonic wave propagating in gas on the gas concentration incorporates a dampproof ultrasonic sensor with a metal or the like deposited by evaporation on the surface of the sealing material. Therefore, this gas concentration measuring instrument is almost not affected by the change of temperature and humidity and can precisely measure gas concentration continuously for a long period of time under high humidity. The ultrasonic sensor is formed fundamentally by an ultrasonic vibrator, a holder and a sealing material. More preferably, this sensor is embedded in a block and sealed with an elastic sealing material and a film of conductive material and/or a nonconductive material is formed on the surface of the sealing material, the elastic sealing material, the vibrating end surface of the ultrasonic sensor and the end surface of the block.

5 Claims, 11 Drawing Figures

MEASURING INSTRUMENT FOR CONCENTRATION OF GAS

BACKGROUND OF THE INVENTION

1. Field of the Invention

This invention relates to instruments for measuring concentrations of gas by ultrasonic wave and particularly to a gas-concentration measuring instrument capable of measuring the concentration of gas with high precision for a long continuous period of time by using a highly dampproof ultrasonic sensor.

2. Description of the Prior Art

There is known an instrument for measuring the concentration of a mixed gas or a single-component gas by utilizing the dependency of the propagation speed of ultrasonic wave on the concentration of gas to be measured as disclosed in, for example, U.S. Pat. No. 4,220,040 issued on Sept. 2, 1980 to the same assignee as the present application. The principle of the measurement will first be described.

The propagation speed of ultrasonic wave in a mixture gas is determined by the constants, concentration and temperature of the mixture gas. In other words, the propagation speed can be expressed by the following equation (1)

$$v^2 = \sum_i C_{pi} X_i / \sum_i C_{vi} X_i \cdot 1/ \sum_i M_i X_i \cdot R \cdot T \quad (1)$$

where v: propagation speed of ultrasonic wave in the mixture gas, $c_{pi}$: specific heat of the object gas i at constant pressure in the mixture gas, $c_{vi}$: specific heat at constant volume of the object gas i in the mixture gas, $M_i$: molecular weight of the object gas i in the mixture gas $X_i$: mole fraction of the object gas i of the mixture gas, R: gas constant, and T: absolute temperature of the mixture gas.

If the mixture gas is assumed to be comprised of air and carbon dioxide $CO_2$, Equation (1) is rewritten as $$v^2 = (C_{pco2}X_{co2} + C_{pair}X_{air})/(C_{vco2}X_{co2} + C_{vair}X_{air}) \cdot R \cdot T \quad (2)$$

The propagation speed of ultrasonic wave was calculated at each concentration of carbon dioxide $CO_2$ by substituting the constants and the absolute temperature, 293° K. of the mixture gas into Equation (2). The results are shown in Table 1 and FIG. 1.

TABLE 1

| $CO_2$ wt % | 0 | 20 | 40 | 60 | 80 | 100 |
|---|---|---|---|---|---|---|
| Mole rate $X_{CO2}$ | 0 | 0.141 | 0.305 | 0.503 | 0.725 | 1.00 |
| v m/sec | 343.07 | 329.66 | 315.56 | 300.30 | 285.04 | 268.25 |

Since $\Sigma X_i = 1$, Equation (2) is alternatively given as the following equation (3):

$$v^2 = \frac{[C_{pair} + (C_{PCO2} - C_{pair})X_{CO2}]}{[C_{vair} + (C_{VCO2} - C_{vair})X_{CO2}]} \quad (3)$$

-continued
$$x \frac{R \cdot T}{[M_{air} + (M_{CO2} - M_{air})X_{CO2}]} = G(X_2, T)$$

Thus, the concentration $X_{CO2}$ is given as the following equation (4):

$$X_{CO2} = F(v, T) \quad (4)$$

In other words, the concentration of the object gas is the function of the propagation speed of ultrasonic wave v and the gas temperature T.

FIG. 2 shows a block diagram of a measuring system according to the present invention, designed on the basis of the above-mentioned theory.

Referring to FIG. 2, an ultrasonic sensor 1 includes a transmitting transducer 2 and receiving transducer 3 disposed opposedly to the transmitting transducer 2. This ultrasonic sensor 1 is mounted within an object gas atmosphere 4 by a proper method. The ultrasonic wave transmitted from transmitting transducer 2 is passed through the ultrasonic wave path 5 containing the object gas and received by the receiving transducer 3. The speed at which the ultrasonic wave passes through the ultrasonic wave path 5 is inversely proportional to the concentration of the object gas. The transmitting transducer 2 comprises an electrostrictive element. A drive amplifier 6 and a negative immitance converter 7 are used to amplify a high-frequency signal generated from a signal generator 8 that is controlled by a feedback oscillation amplifier 10 and to improve the response characteristic. The receiving transducer 3 comprises an electrostrictive element. A preamplifier 9 is used to amplify the high-frequency signal from the receiving transducer 3 and supplies its output to the feedback oscillation amplifier 10. The resistor 11 and the negative immitance converter 12 are used to improve the response characteristic and the sensitivity of the receiving transducer 3.

On the other hand, the frequency, fm of the above-mentioned feedback oscillating system 13 has a relationship with the propagation speed v of the ultrasonic wave that passes through the path 5 within the object mixture gas, i.e., $f_m = k \cdot v/l$ (where l is the distance between the transmitting transducer 2 and the receiving transducer 3 and k is a constant of proportionality). Thus, the frequency $f_m$ of the feedback oscillating system 13 and the stable reference frequency $f_o$ generated from the crystal oscillator element 14 are applied to the mixer 15 where the difference F between $f_m$ and $f_o$ is determined. This value F is converted into a voltage by the frequency-voltage converter 16 and supplied to the compensator 17.

A temperature sensor 18 comprises a thermistor, a temperature measuring resistor or a kind of thermocouple for measuring the temperature of the object gas atmosphere 4. The resulting temperature data is supplied to the compensator 17 for temperature by which the temperature dependency of the propagation speed of ultrasonic wave is eliminated. The temperature-compensated output voltage is indicated on the display unit 19 comprising an analog voltmeter, a digital voltmeter or a recorder.

An example of the measuring method of $CO_2$ gas concentration in a mixture gas comprising three components of air carbon dioxide $CO_2$ and water vapor $H_2O$ according to the present invention will be described in detail with reference to FIGS. 2 and 3.

The gas cylinder 20 containing 100% $CO_2$ gas and a compressor-type air pump 21 respectively supply $CO_2$ gas and air to flow meters 22 and 23 with flow-adjusting valves by which the concentration of $CO_2$ gas is adjusted in advance. A mixing chamber 24 for mixing $CO_2$ gas and air is provided after the flow meters 22 and 23. The $CO_2$/air mixture gas from the mixing chamber 24 is introduced through a lead tube 26 into a measuring chamber 25. A water bath 27 sufficiently deep to immerse the lead tube is provided on the bottom of the measuring chamber 25. The $CO_2$/air mixture gas is blown off from gas blow-off holes provided appropriately in the lead tube 26 through the water bath 27 into the measuring chamber 25. By doing so, the relative humidity in the measuring chamber 25 increases to as high as 95 to 100%. On the upper region of the measuring chamber 25 there is provided a stirring fan 29 which is rotated by a motor 28. This stirring fan 29 serves to make the concentration of the mixture gas in the measuring chamber 25 uniform. The mixture gas is exhausted through a mixture gas outlet pipe 30 to the outside of the measuring chamber 25. The ultrasonic sensor 1 according to the present invention is disposed at an appropriate position in the measuring chamber 25, and connected by a shielded cable 31 to a computation control section 32 which includes the feedback oscillating system 13, the crystal oscillator element 14, the mixer 15, the frequency-voltage converter 16 and the compensator 17. The temperature-compensating temperature sensor 18 including a temperature-measuring resistor is connected through a cable 33 to the compensator 17 of the computation control section 32. The output voltage from the compensator 17 is set at 0 to 20 V against the $CO_2$ gas concentration of 0 to 20% by volume, so that the reading of the output voltage represents the concentration of the $CO_2$ gas. As the display unit 19, a digital voltmeter is used, and the frequency $f_m$ of the feedback oscillating system 13 is monitored by a frequency counter 34. The mixture gas led out through the mixture gas outlet pipe 30 is introduced through an exhaust pipe 36 into an infrared gas analyzer 35 by which the $CO_2$ gas concentration is measured. In addition, a sampling port 37 for the gas chromatograph is provided on the way of the exhaust pipe 36, so that the $CO_2$ gas concentration is checked by the gas chromatograph.

A thermister temperature sensor 39 for measuring the temperature of the mixture gas is provided in the measuring chamber 25, which temperature is monitored by a temperature measuring instrument 40. The measuring chamber 25 is completely sealed except for the mixture gas inlet pipe 41 and the mixture gas outlet pipe 30. Moreover, the measuring chamber 25 is placed within a temperature-variable air constant-temperature oven 42 which can be controlled to within $\pm 0.1°$ C. in order that the temperature within the measuring chamber 25 can be arbitrarily changed.

Thus, on this ultrasonic gas concentration measuring instrument, $CO_2$ gas concentration values changed in the range of 0 to 20% by the flow meters 22 and 23 were actually measured for different temperatures of 27° C., 35° C. and 42° C. within the measuring chamber 25, and the measured data from the infrared ray gas analyzer 35 and the gas chromatograph 38 are shown in Table 2 and FIG. 4.

TABLE 2

| Temp. within chamber (°C.) | Flow meter, set concentration (Vol %) | Gas chromatograph concentration (Vol %) | Ultrasonic concentration meter frequency*1 $f_m$ (Hz) | Ultrasonic concentration meter concentration*2 (Vol %) | Infrared ray gas analyzer concentration (Vol %) |
|---|---|---|---|---|---|
| 27.0 | 0 | 0 | 37.200 | 0 | 0 |
|  | 5 | 5.58 | 36.752 | 5.6 | 5.6 |
|  | 10 | 10.36 | 36.370 | 10.4 | 10.5 |
|  | 14 | 14.14 | 36.075 | 14.1 | 14.1 |
|  | 17 | 17.16 | 35.835 | 17.1 | 17.2 |
| 35.0 | 0 | 0 | 37.536 | 0 | 0 |
|  | 4 | 4.07 | 37.205 | 4.1 | 4.2 |
|  | 11 | 11.04 | 36.652 | 11.0 | 11.2 |
|  | 12 | 12.48 | 36.535 | 12.5 | 12.8 |
|  | 17 | 16.63 | 36.209 | 16.6 | 16.9 |
| 42.0 | 0 | 0 | 37.870 | 0 | 0 |
|  | 3 | 3.37 | 37.596 | 3.4 | 3.4 |
|  | 8 | 7.62 | 37.265 | 7.6 | 7.9 |
|  | 12 | 12.19 | 36.890 | 12.2 | 12.6 |
|  | 16 | 15.84 | 36.606 | 15.8 | 16.4 |

*1Frequency of ultrasonic wave gas concentration measuring system.
*2Reading on ultrasonic wave gas concentration measuring system.

From Table 2 and FIG. 4, it is seen that the frequency fm of the feedback oscillating system of the ultrasonic wave gas concentration measuring system according to the present invention represents a linear characteristic against the concentration indicated by the gas chromatograph and the infrared ray gas analyzer, and that the concentration indicated by the ultrasonic wave gas concentration measuring system is sufficiently identical to the concentration indicated by the gas chromatograph and the infrared ray gas analyzer.

Although the foregoing description concerns an embodiment of the method and system for measuring the gas concentration according to the present invention including the three gas component of $CO_2$, air and $H_2O$, the present invention is not limited to such a composition of the mixture gas.

The ultrasonic sensors will hereinafter be described which are respectively used in the ultrasonic-wave transmitting element and the ultrasonic-wave receiving element of the ultrasonic wave gas concentration measuring system. The sensors including the elements have the same structure as that of the conventional one. That is, the sensor of this structure is formed by an ultrasonic transducer (for example, piezo-electric ceramic such as PZT) having silver electrodes fused together and which is attached to a plate or holder (made of, for example, metal or plastics). This type of ultrasonic sensor has so far been used for transmission or reception of ultrasonic wave in the measure/control ultrasonic equipment. This type of sensor has a drawback that the electrodes on the surface of the PZT or the like, for example, silver electrodes are easy to be electrically corroded in the presence of water vapor, thus often making it difficult to correctly convert an ultrasonic-wave signal to an electric signal and vice versa. Thus, in order to prevent the electrodes on the ultrasonic transducer from being electrically corroded, a sealing material such as silicone resin, epoxy resin or polyurethane has been utilized for preventing water vapor from entering into the holder. Nevertheless, even the ultrasonic sensor with its ultrasonic transducer attached to the holder and sealed with a sealing material was erroded by gradual intrusion of water vapor after it was continuously operated for as long a time as one to ten years in the atmosphere of 80 to 100% humidity. There is another countermeasure against the electric corrosion which employs a metal holder and seals it by welding. However, the adhesive resin with which the ultrasonic transducer is attached to the metal holder is easy to be deteriorated by heat upon welding.

The prior art will be described in more detail with reference to the accompanying drawings. FIG. 8 shows an example of the conventional ultrasonic sensor. FIG. 8a is a cross-sectional view of an ultrasonic sensor 59 and FIG. 8b is an enlarged cross-sectional view of an ultrasonic transducer 45 (made of, for example, a piezo-electric ceramic material such as PZT, or a resin material having a piezo-electric characteristic) and its peripheral portion.

As shown in FIG. 8b, the ultrasonic transducer 45 is attached with electrodes 60 and 61 and bonded to a holder 44 (made of for example, metal or resin) with an adhesive agent 62 having a good characteristic for propagation of the ultrasonic wave. The electrodes 60 and 61 are connected through wires 46 and 47 to terminals 48 and 49 which are fastened to a base 50 (made of for example, phenol resin laminated board or epoxy laminated board) as shown in FIGS. 8a and 8b. The holder 44 is sealed by covering the base with a sealing material 51. This structure, however, has a drawback that when it is continuously operated for as long a time as, for example, one year to 10 years in the atmosphere including water vapor, water vapor enters into the holder 44 through the sealing material 51, making the electrodes 60 and 61 be electrically corroded so that the ultrasonic wave cannot be correctly transmitted and received.

SUMMARY OF THE INVENTION

Accordingly, it is an object of this invention to provide a gas concentration measuring instrument having an ultrasonic sensor used for the elements transmitting and receiving an ultrasonic wave, and which is capable of precisely measuring gas concentration continuously for a long time by forming on the ultrasonic sensor surface a thin film against the effect of water vapor.

According to this invention, there is provided a gas concentration measuring system using a dampprooftype ultrasonic sensor which basically comprises an ultrasonic transducer, a holder and a sealing material and which is characterized in that a film of an electrically conductive material and/or an electrically, nonconductive material is formed on the surface of the sealing material.

EFFECT OF THE INVENTION

According to this invention, a thin film is formed on the sealing material of a conventional ultrasonic sensor, thereby greatly increasing the moisture resistance of the conventional ultrasonic sensor. Thus, the ultrasonic sensor used in the ultrasonic gas concentration measuring instrument can be continuously operated for a long period of time in the atmosphere including water vapor. An accelerated test was made on the ultrasonic sensor with the thin film formed, to be used in the present invention and the conventional ultrasonic sensor, and the results are shown in FIG. 10. In this test, each ultrasonic sensor was immersed in 60° C. warm water and applied with a DC voltage. In FIG. 10, the ordinate, 66 indicates the insulating resistance expressed in megohms $M\Omega$ and the abscissa, 65 is the time for which the test was made. From the comparison between a curve 63 for the ultrasonic sensor with thin film to be used in the present invention and a curve 64 for the conventional ultrasonic sensor in FIG. 10, it will be understood that the sensor to be used in the present invention has no change of its insulating resistance, or is excellent in its moisture resistance. Moreover, the ultrasonic sensor or shown in FIGS. 5 to 7 is embedded in the block 67 and a thin film is formed on the elastic sealing material 75, block 67 and vibrating and surface 71, thereby enabling its moisture resistance to be further increased.

Therefore, the ultrasonic gas concentration measuring instrument using the ultrasonic sensor of which the moisture resistance is greatly increased is almost not affected by the change of temperature and moisture and can precisely measure gas concentration continuously for a long period of times under high-humidity atmosphere. This feature is extremely useful for industry.

BRIEF DESCRIPTION OF THE DRAWINGS

FIG. 8b is an enlarged cross-sectional view of the ultrasonic transducer 45 and its peripheral portion of the sensor of FIG. 8a.

DESCRIPTION OF THE PREFERRED EMBODIMENTS

The present invention will be described with reference to the accompanying drawings.

Figure 1:
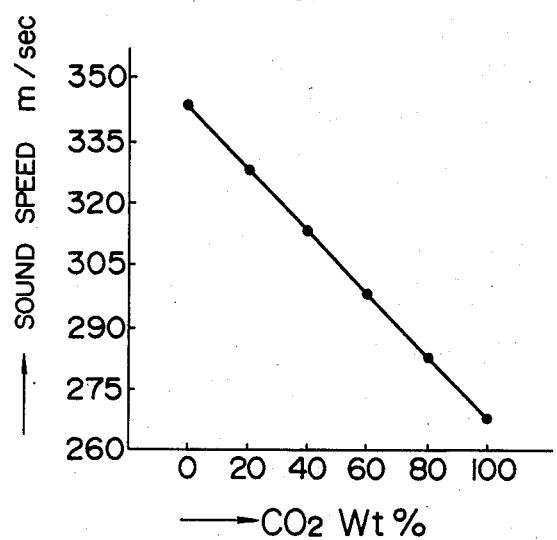
FIG. 1 is a graph showing a relation between $CO_2$ gas concentration and propagation speed of ultrasonic wave.
Figure 2:
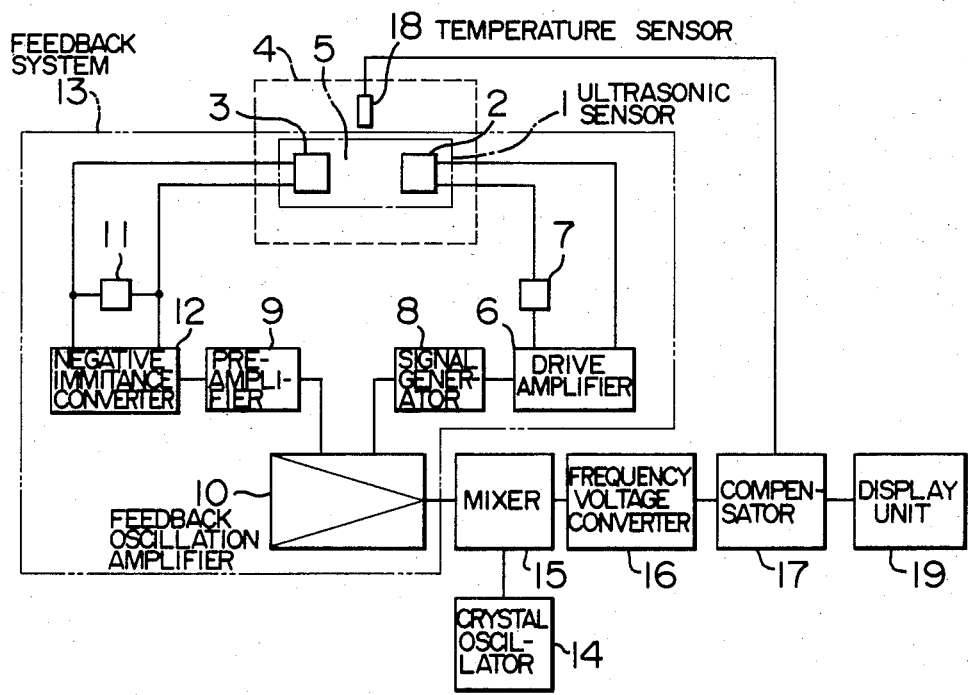
FIG. 2 is a block diagram of an example of the measuring system.
Figure 3:
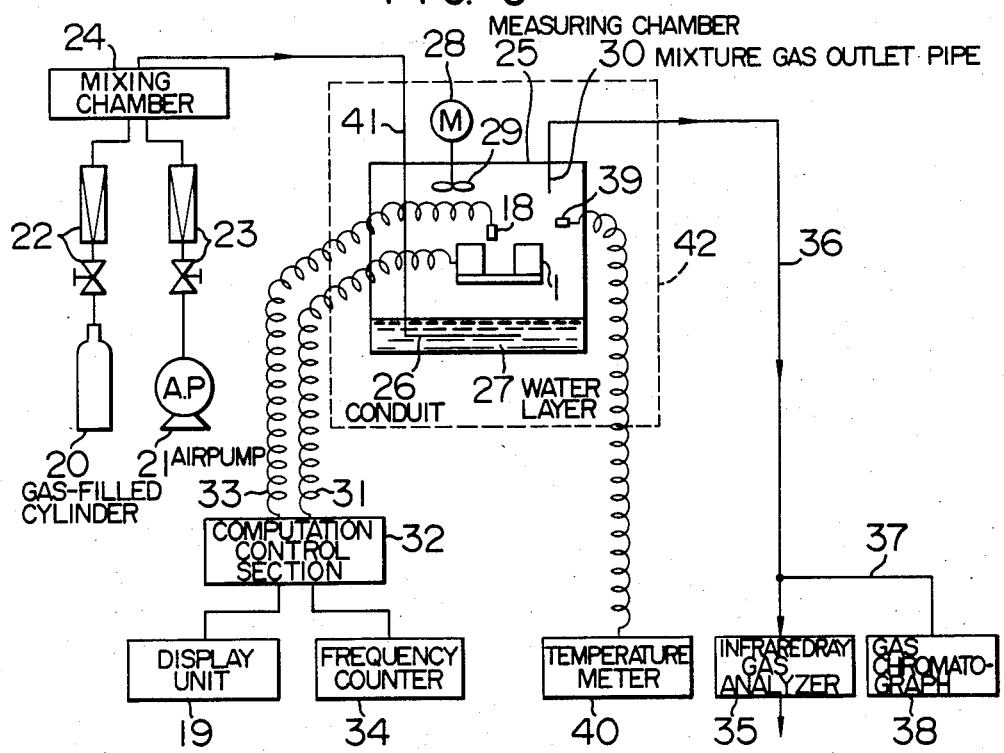
FIG. 3 shows one example of the method for measuring $CO_2$ gas concentration on a gas concentration measuring system.
Figure 4:
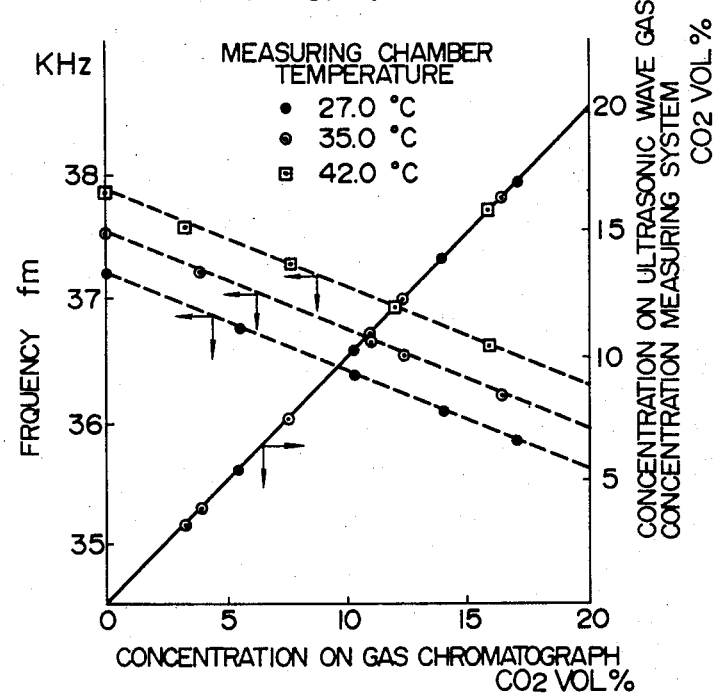
FIG. 4 graphically represents the data of Table 2.
Figure 5:
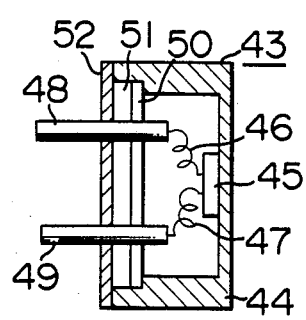
FIGS. 5 to 7 are cross sectional views of examples of the ultrasonic sensor to be used in this invention.
Figure 6:
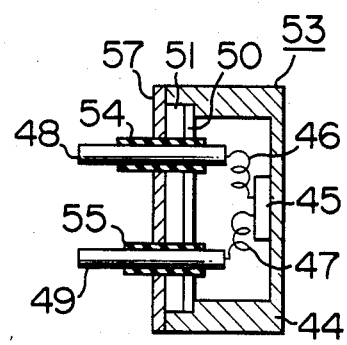
Figure 7:
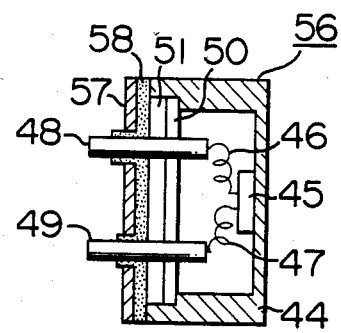
Figure 8A:
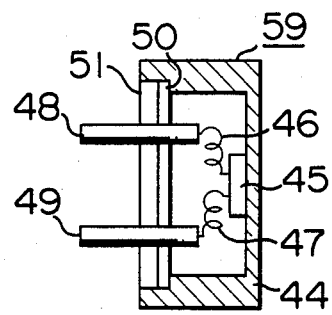
FIG. 8a is a cross-sectional view of a conventional ultrasonic sensor.
Figure 8B:
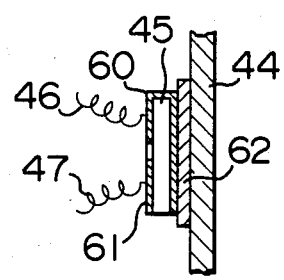

FIGS. 5 to 7 are cross-sectional side views of the ultrasonic sensors 43, 53 and 56 to be used in this invention. The basic structure of each sensor is the same as that of the conventional ultrasonic sensor shown in FIG. 8. The ultrasonic transducer 45 is provided with the electrodes 60 and 61 and attached to the holder 44 with the adhesive 62 as shown in FIG. 8b. The electrodes 60 and 61 are connected through the wires 46 and 47 to the terminals 48 and 49. The terminals 48 and 49 are fixed to the base 50 over which the sealing material 51 is covered to seal the holder 44.

FIG. 5 shows an ultrasonic sensor 43 with a thin film 52 formed on the surface of the sealing material 51. The material for the thin film 52 may be a nonconductive material, particularly SiO, SiO$_2$ or a fluorine-based resin such as polytetorafluoroethylene which can be deposited to be thin by for example, vacuum evaporation, sputtering, or ion plating. The thickness of the film should be in the range from 500Å to 5000Å, preferably from 1500Å to 3000Å. Since the thin film 52 is non-conductive the portions of the terminals 48 and 49 which are projected through the sealing material 51 out of the holder 44 must be covered by, for example, Teflon (trade name) tape or the like in order that the thin film 52 is not deposited thereon except the surface of the sealing material 51.

FIG. 6 shows an ultrasonic sensor 53 with insulating films 54 and 55 formed on the terminals 48 and 49 which otherwise would be made in contact with the thin film 57 which is formed on the surface of the sealing material 51. The material for the thin film 57 must be an electrically conductive material which can be formed by, for example, vacuum evaporation, sputtering or ion plating, particularly Al, An, Pb, Cu, titanium alloy, Ni, Cr, MoS$_2$, or MgF$_2$. The thickness of the film is in the range from 500Å to 5000Å, preferably, from 1500Å to 3000Å. Since the thin film 57 is electrically conductive, the insulating films 54 and 55 are formed on the areas of the terminals 48 and 49 which otherwise would be made in contact with the base 50 sealing material 51 and thin film 57. The portions of the terminals 48 and 49 which are projected through the sealing material 51 out of the holder 44 must be covered by, for example, Teflon (trade name) tape or the like in order that the thin film 57 is not deposited thereon except the surface of the sealing material 51.

FIG. 7 shows an ultrasonic sensor 56 with a thin film 58 formed on the surface of the sealing material 51 and on the areas of the surfaces of the terminals 48 and 49 which otherwise would be made in contact with the thin film 57 formed on the thin film 58. The material of the thin film 58 must be any insulating material which can be formed by vacuum evaporation, sputtering, or ion plating, particularly preferably an insulating material having coefficient of linear expansion between those of the sealing material 51 and thin film 57. The thickness of the thin film 58 is in the range from 100Å to 4000Å, preferably 500Å to 1000Å. Also, when the thin films 58 and 57 are formed, the portions of the terminals 48 and 49 which are projected through the sealing material 51 out of the holder 44 are covered by, for example, Teflon (trade name) tape in order that thin film 58 cannot be deposited thereon except the areas of the surfaces of the terminals 48 and 49 which otherwise would be made in contact with the thin film 57, and that the thin film 57 cannot be deposited thereon except part of the thin film 58 formed on the areas of the surfaces of the terminals 48 and 49.

The materials of the ultrasonic transducer 45, holder 44, base 50 and sealing material 51 for the sensor to be used in the present invention may be the same as those for the conventional sensor. That is, the material for the ultrasonic transducer may be a piezo-electric ceramic material such as PZT, a resin having a piezo-electric characteristic, the material for the holder may be any metal or plastic material, the material for the base may be a laminated board of phenol resin, epoxy resin or the like, and the sealing material may be silicone resin, epoxy resin, polyurethane or the like.

Figure 9:
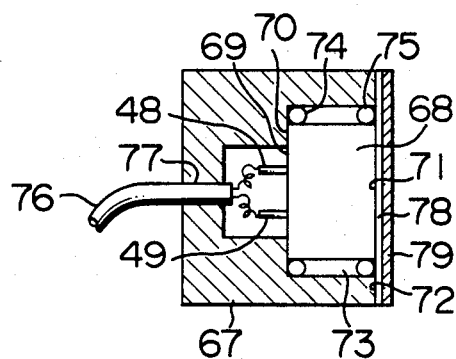
FIG. 9 is a cross-sectional view of an example of the ultrasonic wave sensor to be used in this invention.
Figure 10:
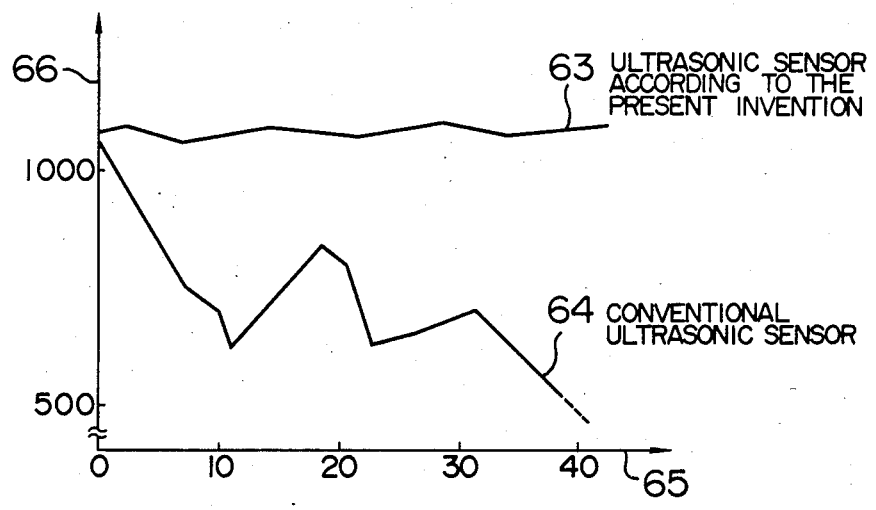
FIG. 10 is a graph showing the results of the damp-proof test of the conventional sensor and the sensor to be used in this invention.

FIG. 9 shows an ultrasonic sensor 68 embeded in a block 67, this sensor being the same as mentioned with reference to FIGS. 5 to 7. This block can improve the dampproof. The block 67 shown in FIG. 9 is made of a corrosion-resisting metal such as aluminum or stainless steel or a synthetic resin. An end surface 69 of the ultrasonic sensor 68 on the terminals 48, 49 side is set in position by a sensor supporting portion 70 of the block 67 so that a vibration end surface 71 of the ultrasonic sensor 68 is substantially flush with a block end surface 72 of the block 67. In an annular gap 73 between the ultrasonic sensor 62 and the block 67 is inserted elastic sealing materials 74 and 75 such as silicone resin or rubber which can absorb the ultrasonic vibration of the ultrasonic sensor 68, thereby fixing the ultrasonic sensor 68 to the block 67. A cable 76 is a two-core cable for transmission and reception of a high-frequency signal for ultrasonic wave to and from the terminals 48 and 49 of the ultrasonic sensor 68. This cable 76 is connected to the terminals 48 and 49 through an aperture 77 bored in the block 67 on the left end surface. The gap between the block 67 and the cable 76 is filled for sealing with a screw bush or a high moisture-resistant resin such as polybutadiene polyvinylidene chloride.

A thin film 78 and/or a thin film 79 are formed on the surface of the elastic sealing material 75, the vibrating end surface 71 and the block end surface 72 which otherwise would be exposed to the open air. The material for the thin film 78 must have a high adhesion to the elastic sealing material 75. For example, when the elastic sealing material 75 is a silicone resin, it must be formed by vacuum evaporation, sputtering, ion plating or the like and it is preferably a nonconductive thin film of SiO, SiO$_2$ or the like. The material for the thin film 79 is necessary to have a good adhesion to the thin film 78 of SiO, SiO$_2$ or the like, the block 67 and the vibration end surface 71, to be formed by vacuum evaporation, sputtering, ion plating or the like and to cause few pinholes in itself. Particularly, the material for this thin film 79 should be preferably a conductive thin film such as Al, Au, Pb, Cu, titanium alloy, Ni, Cr, MoS$_2$ or MgF$_2$. The thickness of the thin film 78 is in the range from 100Å to 4000Å, preferably from 500Å to 1000Å. The thickness of thin film 79 is in the range from 500Å to 5000Å, preferably from 1500Å to 3000Å. The total thickness of the thin films 78 and 79 is in the range from 1000Å to 5000Å, preferably from 2000Å to 4000Å.

While in this embodiment, two thin films 78 and 79 are formed, either of the films 78 or 79 may be formed depending on the combination of the materials of the elastic sealing material 75, block 67 and vibration end surface 71.

We claim:

1. A gas concentration measuring instrument comprising a signal generator controlled by a feedback amplifier, a drive amplifier for amplifying a high-frequency signal generated from said signal generator, an ultrasonic sensor including an ultrasonic-wave transmitting element formed of an electrostrictive type transducer for converting the high-frequency signal amplified by said drive amplifier to an ultrasonic wave and transmitting the ultrasonic wave and an ultrasonic-wave receiving element formed of an electrostrictive transducer for receiving said ultrasonic wave and converting the same to an electrical signal, a feedback oscillating system including a negative immitance converter connected between said ultrasonic wave transmitting element and the drive amplifier, a resistance and a negative immitance converter connected in parallel with said ultrasonic receiving element, a preamplifier connected to the input of the feedback amplifier, and an computation output system including a mixer for producing the difference between a frequency from the feedback oscillating system and a reference frequency from a crystal resonator, a frequency-voltage converter for converting the difference frequency from said mixer to a voltage and a compensator for calculating a gas concentration from the output from said frequency-voltage converter and the temperature information detected by a temperature sensor, characterized in that said ultrasonic sensor is a dampproof ultrasonic sensor which is formed fundamentally by an ultrasonic vibrator, a holder, and a sealing material on the outer surface of which is deposited at least one film formed by vacuum evaporation, sputtering, or ion plating of at least one material selected from the group consisting of Al, An, Ph, Cu, titanium alloy, Ni, Cr, $MoS_2$, $MgF_2$, SiO, and $SiO_2$, and said at least one film having a thickness in the range of from 500Å to 5000Å.

2. A gas concentration measuring instrument according to Claim 1, wherein said film deposited on the sealing material of the ultrasonic sensor is formed by a film of a nonconductive material deposited on the sealing material and a film of a conductive material deposited on said nonconductive material film.

3. A gas concentration measuring instrument according to Claim 1, wherein said ultrasonic sensor is embeded in a block and a film of a nonconductive material and/or a conductive material is formed on an elastic sealing material, a vibrating end surface of the ultrasonic sensor and an end surface of the block.

4. A gas concentration measuring instrument according to Claim 2, wherein said ultrasonic sensor is embeded in a block and a film of a nonconductive material and/or a conductive material is formed on an elastic sealing material, a vibrating end surface of the ultrasonic sensor and an end surface of the block.

5. A gas concentration measuring instrument according to claim 1 wherein said at least one film includes a film having a thickness in the range from 1500Å to 3000Å.

* * * * *